US012588877B2

(12) United States Patent
Alexis et al.

(10) Patent No.: US 12,588,877 B2
(45) Date of Patent: Mar. 31, 2026

(54) BORE TUBE OF A RADIOTHERAPY DEVICE

(71) Applicant: Elekta Limited, Crawley (GB)

(72) Inventors: Henrik Alexis, Crawley (GB); Thomas Pihl, Crawley (GB); Erik Carlander, Crawley (GB); Eldered Kjell, Crawley (GB)

(73) Assignee: Elekta Limited, Crawley (GB)

( * ) Notice: Subject to any disclaimer, the term of this patent is extended or adjusted under 35 U.S.C. 154(b) by 214 days.

(21) Appl. No.: 18/495,047

(22) Filed: Oct. 26, 2023

(65) Prior Publication Data

US 2024/0138782 A1     May 2, 2024

(30) Foreign Application Priority Data

Oct. 26, 2022     (GB) ..................................... 2215818

(51) Int. Cl.
| | |
|---|---|
| *A61N 5/10* | (2006.01) |
| *A61B 6/03* | (2006.01) |
| *A61B 6/40* | (2024.01) |

(52) U.S. Cl.
CPC ............ *A61B 6/032* (2013.01); *A61B 6/4085* (2013.01)

(58) Field of Classification Search
CPC ......... A61B 6/032; A61B 6/4085; A61B 6/44; A61N 2005/1061; A61N 2005/1094; A61N 5/1081; A61N 5/1001; A61N 5/103; A61N 5/1048; A61N 5/1049; A61N 5/1077; A61N 2005/1092; A61N 2005/1091; A61N 2005/1095
See application file for complete search history.

(56) References Cited

U.S. PATENT DOCUMENTS

| | | | |
|---|---|---|---|
| 2010/0177867 A1 | 7/2010 | Kozelj et al. | |
| 2013/0266116 A1 | 10/2013 | Abenaim et al. | |
| 2015/0224341 A1 | 8/2015 | Vahala et al. | |
| 2015/0265229 A1* | 9/2015 | Maki ..................... A61B 6/032 |
| | | | 378/197 |
| 2016/0374632 A1 | 12/2016 | David | |
| 2020/0137861 A1 | 4/2020 | Imaizumi et al. | |
| 2020/0205752 A1 | 7/2020 | Zhang et al. | |
| 2021/0138270 A1 | 5/2021 | Hale | |

FOREIGN PATENT DOCUMENTS

| | | |
|---|---|---|
| GB | 2590648 A | 7/2021 |
| WO | WO-2020106523 A1 | 5/2020 |

OTHER PUBLICATIONS

"United Kingdom Application Serial No. 2215818.2, Examination Report dated Apr. 13, 2023", (Apr. 13, 2023), 5 pgs.
"European Application Serial No. 23204748.0, European Search Report dated Mar. 11, 2024", (Mar. 11, 2024), 7 pgs.
"British Application No. 2215818.2, Examination Report dated Dec. 19, 2024", (Dec. 19, 2024), 3 pgs.
"British Application No. 2510508.1, Search Report dated Sep. 3, 2025", Sep. 3, 2025, 5 pgs.

* cited by examiner

*Primary Examiner* — Courtney D Thomas
(74) *Attorney, Agent, or Firm* — Schwegman Lundberg & Woessner, P.A.

(57) ABSTRACT

A radiotherapy device may comprise a rotatable gantry and a bore tube defining a bore. The bore tube may comprise a first section formed of a first material and a second section formed of a second material. The first section may be configured to minimally attenuate an imaging beam, while the second section may be configured to meet further requirements of the bore tube.

18 Claims, 3 Drawing Sheets

BORE TUBE OF A RADIOTHERAPY DEVICE

CLAIM FOR PRIORITY

This application claims the benefit of priority of British Application No. 2215818.2, filed Oct. 26, 2022, which is hereby incorporated by reference in its entirety.

TECHNICAL FIELD

This disclosure relates to radiotherapy, and in particular to the bore tube of a radiotherapy device.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device can comprise a gantry which supports a beam generation system, or other source of radiation, which is rotatable around a patient. For example, for a linear accelerator (linac) device, the beam generation system may comprise a source of radio frequency energy, a source of electrons, an accelerating waveguide, beam shaping apparatus, etc. The gantry may also support a source of imaging radiation, for example a source of kilovolt (kV) X-ray imaging radiation, and an imaging detector.

It is desirable to protect patients from the rotating gantry and other components of the radiotherapy device attached to the rotating gantry during radiotherapy treatment and imaging processes. This is of increased importance for gantries that rotate at high speed. Patients can be protected by a shield formed around the beam generation and imaging components, and this shield may define a bore into which a patient can be moved for treatment and/or imaging. The shield, or bore tube, acts as a physical barrier between the patient and fast-moving components of the radiotherapy device. The bore tube may be cylindrical in shape.

During imaging, the imaging radiation beam must pass through the bore tube, through the patient and then through the bore tube once more to reach the detector. The material of the bore tube attenuates the radiation beam as it passes through, reducing the resulting image quality. Since the beam must pass through the bore tube twice before detection, any attenuation by the bore tube material is effective two-fold. Additionally, any artefacts or variations in the bore material will reduce the accuracy or quality of the image. Increasing the beam intensity to compensate for this exposes the patient to a larger dose which may be dangerous and excessive.

Therefore, it would be desirable to increase the transparency of the bore tube to the imaging radiation, in order to minimise attenuation and degradation and thereby maximise image quality.

Bore tubes may be required to meet a number of requirements, including being adequately transparent to imaging radiation and providing adequate protection to the patient. Forming a bore tube from a material with increased transparency may make it more difficult to meet other requirements of the bore tube. In addition, such a material may require strict engineering and manufacturing processes with tight tolerances, along with rigorous testing. This may be labour-intensive and expensive. It would be desirable to provide increased transparency of a bore tube while meeting other requirements of the bore tube and limiting engineering complexity.

SUMMARY

According to an aspect of the present disclosure, a radiotherapy device may comprise a rotatable gantry and a bore tube defining a bore. The bore tube may comprise a first section formed of a first material and a second section formed of a second material.

BRIEF DESCRIPTION OF THE FIGURES

Specific embodiments are now described, by way of example only, with reference to the drawings, in which.

DETAILED DESCRIPTION

In presently disclosed systems, an improved bore tube design for a radiotherapy device is provided. In order to improve imaging quality, the bore tube comprises a first section and a second section. The first section can be configured to minimally attenuate the imaging beam, whilst the second section can optionally be configured to meet further requirements of the bore tube.

In the following, application of radiotherapy and/or imaging radiation to a patient will be referred to in most detail in order to provide clarity of explanation. Such use of the term patient should not be interpreted to limit application of the present disclosure. The present disclosure provides means that can be used to apply radiotherapy to any subject. The terms patient and subject may be used interchangeably herein.

The implementations of the present disclosure may be any radiotherapy device, for example a linac device.

FIG. 1

Figure 1:
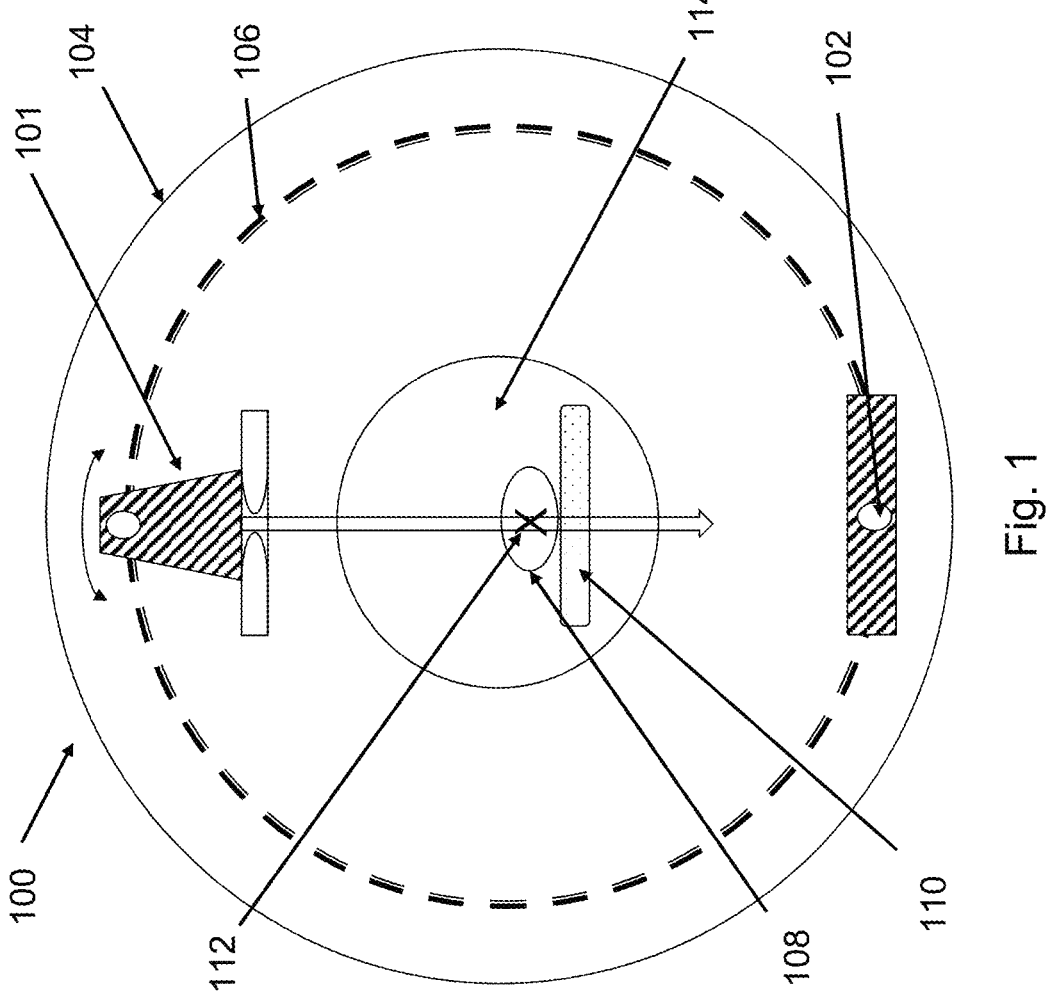
FIG. 1 depicts a radiotherapy device according to the present disclosure.

FIG. 1 depicts a radiotherapy device 100 suitable for delivering, and configured to deliver, a beam of radiation to a patient during radiotherapy treatment. The arrangement described should be considered as providing one or more examples of a radiotherapy device and it will be understood that other arrangements are possible and can be used to perform the methods described herein. The Figure shows a cross-section through a radiotherapy device 100 comprising a radiation source 101 and a detector 102 attached to a rotatable ring-shaped gantry 104. For any reference made herein to a gantry, it can be assumed that the gantry may be a rotatable ring shaped gantry. The radiation source 101 and the detector 102 may be fixed to the gantry 104 and may rotate with the gantry. The gantry may comprise a circular support track 106.

FIG. 1 also depicts a patient 108 on a table 110. The table 110 may be moved longitudinally relative to the gantry 104 (i.e. away from the plane of the gantry 104), for example to aid positioning of the patient 108. In some examples, the table 110 may be moved along other translational axes (e.g. in the plane of the gantry) and/or rotational axes. The patient table may also be referred to as a moveable or adjustable couch or support surface.

The table 110 can be used to move a patient 108, or other subject, into a bore 114 when radiotherapy is to commence. The bore 114 lies through the central hole of the ring-shaped gantry 104. The patient table 110 is configured to move between a first position substantially outside the bore 114, and a second position substantially inside the bore 114. In the first position, a patient 108 or subject can mount the patient table. The table 110, and patient 108, can then be moved inside the bore 114, to the second position, in order for the patient 108 to be treated using the radiotherapy device. The movement of the patient table 110 is effected and controlled by a patient table actuator (not shown in FIG. 1), which may be described as an actuation mechanism. The actuation mechanism is configured to move the patient table 110 in a direction parallel to, and defined by, the central axis of the bore. The terms subject and patient 108 are used interchangeably herein such that the patient table 110 may also be described as a subject table.

As radiation is applied to the patient 108, for example according to a treatment plan, the radiation source 101 and the detector 102 may rotate together with the gantry 104 and/or around the circular support track 106 such that they are always arranged 180° from one another. The radiation source 101 may direct radiation towards the patient 108 from various angles around the patient 108 in order to spread out the radiation dose received by healthy tissue to a larger region of healthy tissue while building up a prescribed dose of radiation at a target region. As shown in FIG. 1, radiation may be emitted in a plane which is perpendicular to the axis of rotation of the radiation source 101. Thus, radiation may be applied to a radiation isocentre 112 at the centre of the gantry 104 regardless of the angle to which the radiation source 101 is rotated about the gantry 104.

A treatment delivery may comprise rotation of the radiation source 101 and application of radiation by the radiation source 101, for example according to a treatment plan. In a treatment delivery, the rotation of the radiation source 101 may be through a predetermined angle. The radiation source 101 may rotate in a continuous or substantially continuous treatment arc, and/or may rotate to and pause at a plurality of discrete angles. The treatment plan comprises a prescribed dose (e.g. a clinically-prescribed dose) for the target region.

In some examples, the radiotherapy device 100 may comprise one or more additional panels and/or sources and/or detectors. The radiotherapy device 100 may comprise one or more imaging devices, which may comprise a source and a detector. This source and detector may be fixed to the gantry 104 and may rotate with the gantry 104, and/or may rotate around the circular support track 106, such that they are always 180° from one another. This source and detector may be disposed in the plane of the gantry 104 or may be projected a longitudinal distance from the gantry 104, for example on additional support arms. The source may be a source of X-rays, for example an X-ray tube. The detector may be configured to detect X-rays. The source may be configured for kV imaging, i.e. may emit kV X-rays. The detector may be configured to detect the kV X-rays. As used herein, any of the above-described features may be referred to as components of the radiotherapy device.

In some embodiments, the radiotherapy device 100 may be configured to provide computed tomography (CT) and/or cone-beam computed tomography (CBCT). The radiotherapy device 100 may comprise components configured to perform MV imaging and may comprise components configured to perform kV imaging. The radiation source 101 of the radiotherapy device 120 may emit MV radiation for treating the patient. This radiation source 101 may be used as the MV beam source for MV imaging. The detector 102 may be disposed diametrically opposite the radiation source 101, with the patient 108 therebetween. As described above, the radiotherapy device may comprise a kV imaging source, and a kV detector arranged diametrically opposite to the kV imaging source with the patient 108 therebetween. The kV imaging source and the kV detector may be arranged in a different plane (i.e. at a different angle) to the treatment beam source and the MV detector. In some embodiments, alternatively or additionally, the radiotherapy device 100 may be configured for MR imaging. The radiotherapy device 100 may comprise an MR imaging apparatus configured to generate MR images of the patient 108.

The radiotherapy device 100 may comprise a controller (not shown). The controller may be a computer, processor, or other processing apparatus. The controller may be formed by several discrete processors; for example, the controller may comprise a processor for each of the various individual components of the radiotherapy device 100 as described herein. The controller may be communicatively coupled to a memory, e.g. a computer readable medium. The controller may be communicatively coupled to one, multiple or all of the various individual components of the radiotherapy device 100 as described herein. As used herein, the controller may also be referred to as a control device.

FIG. 2

Figure 2:
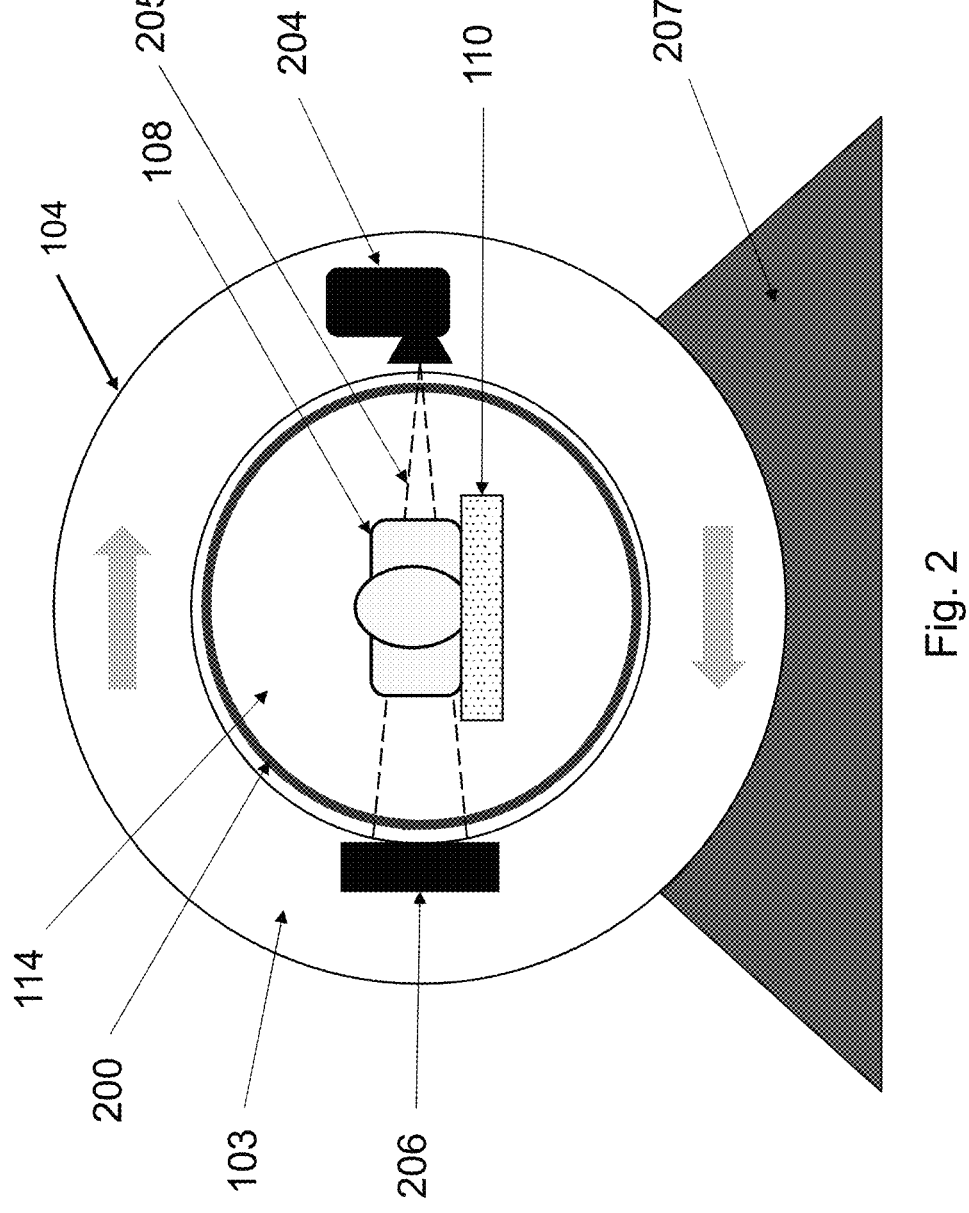
FIG. 2 depicts a rotatable gantry and bore tube of a radiotherapy device according to the present disclosure.

FIG. 2 depicts a rotatable gantry and bore tube according to the present disclosure. The radiotherapy device includes a rotatable ring gantry 104, and a bore tube 200. The rotatable ring gantry 104 rotates relative to a fixed, stationary support structure 207. The support structure 207 may be a fixed, stationary structure configured to support other components of the radiotherapy device such as the rotatable ring gantry.

A bore tube 200 is shown in FIG. 2. The bore tube 200 defines the bore 114. The bore 114 lies through the central hole of the ring-shaped gantry 104. The bore tube 200 covers an inner surface of the radiotherapy device. The bore tube 200 may be a cylindrical cover. The bore tube 200 may be referred to as an inner cover. In some examples, the ring-shaped gantry 104 may be described as comprising the bore tube 200. The bore tube 200 may attenuate or otherwise affect an imaging radiation beam, reducing image quality.

The purpose of the bore tube 200 is to cover the components of the radiotherapy device and to shield the patient from the components of the rotating gantry 104, as further described below.

One or more components of the radiotherapy device 100 may move around a patient 108 on the gantry 104 and/or on the circular support track 106. Alternatively, or in addition, the table 110 may move relative to the gantry 104. These movements may occur prior to or during radiotherapy treatment. In other words, there exists a risk of a patient and/or an operator of the radiotherapy device and/or items such as clothing coming into contact with the fast-moving components of the radiotherapy device and/or the gantry. Such contact may be dangerous for several reasons: the patient and/or clinician may be injured, components of the radiotherapy device may be damaged, and application of radiotherapy could be disrupted, potentially causing an inaccuracy in treatment. Therefore, there is a need to provide protection between the moving components of the radiotherapy device and/or gantry, and the patient and/or clinician. This protection is provided by the bore tube 200. It is further advantageous to provide a bore tube with no slits/ gaps so that there is a physical barrier provided along the whole length of the bore.

The radiotherapy device may comprise an imaging apparatus. A patient 108 may be moved into the bore 114 for radiotherapy treatment and/or imaging processes. The patient is supported by a support structure 110, also referred to herein as a patient table. The table 110 is configured to move between a first position substantially outside the bore tube 200, and a second position substantially inside the bore tube 200. In the first position, a patient or subject can mount the patient table 110. The table 110, and patient 108, can then be moved inside the bore tube 200, to the second position, in order for the patient to be treated using the radiotherapy device, and/or imaged using imaging apparatus. The patient table may configured such that movement between the first position and the second position may be executed automatically, i.e. without manual input and/or supervision from a clinician.

The bore tube 200 extends along a central axis of the bore 114, longitudinal relative to the gantry (i.e. towards/away from the plane of the gantry 104). In other words, the bore tube 200 extends into/out of the page as shown in FIG. 2.

The rotatable gantry 104 may support the imaging apparatus. The imaging apparatus may comprise a source of imaging radiation 204 and a detector 206. The source of imaging radiation 204 and the detector 206 may be each be located at a greater diameter than the bore tube 200, i.e. further from the central axis of the gantry 104/bore 114 than the bore tube 200, and may be located diametrically opposite each other (180 degrees apart). The source of imaging radiation 204 is configured to emit an imaging radiation beam 205 which may be suitable for X-ray imaging. The source 204 may be a source of kilovolt (kV) X-rays, for example a kV tube. The detector may be configured to detect kV X-rays. In some embodiments, the source may be a source of megavolt (MV) X-rays and the detector may be configured to detect MV X-rays. In some embodiments, the radiotherapy device 100 according to FIGS. 1 and 2 may comprise more than one imaging device. In some embodiments, one or more imaging devices may be configured such that the source and detector are fixed to the gantry and rotate with the gantry, and/or rotate around a circular support track (not shown in FIG. 2), such that they are always 180° from one another.

In the embodiment shown in FIG. 2, in order to reach an imaging detector 206, the imaging radiation beam 205 must pass through the bore tube 200 to enter the bore 114, then pass through patient 108, then pass through the bore tube 200 again to exit the bore 114. In other words, the imaging radiation must pass through the bore tube 200 twice before detection. This means that any attenuation of the beam 205 caused by the material of the bore tube 200 is effective twofold. It is therefore advantageous to ensure the section of the bore tube 200 through which the imaging radiation passes causes minimal attenuation. This will improve the quality of the image obtained. In other words, the section of the bore tube 200 through which the imaging radiation passes should be completely, mostly or predominantly transparent to imaging radiation. Additionally, any artefacts and/ or (spatial) variations in the material of the bore tube 200 will further distort, degrade or otherwise affect the image. It is advantageous to ensure the section of the bore tube 200 through which the imaging radiation passes contains few or no artefacts and/or variations. This will improve the quality of the image obtained.

In some embodiments, during a treatment and/or imaging procedure, the imaging beam may be at least one of a kV or a MV imaging beam. It is advantageous to configure the bore tube such that it can withstand substantial radiation doses.

It will be appreciated that there is a need for an improved bore tube. The present disclosure provides an improved bore tube and provides means to improve image quality for a radiotherapy device comprising a bore.

FIG. 3

Figure 3:
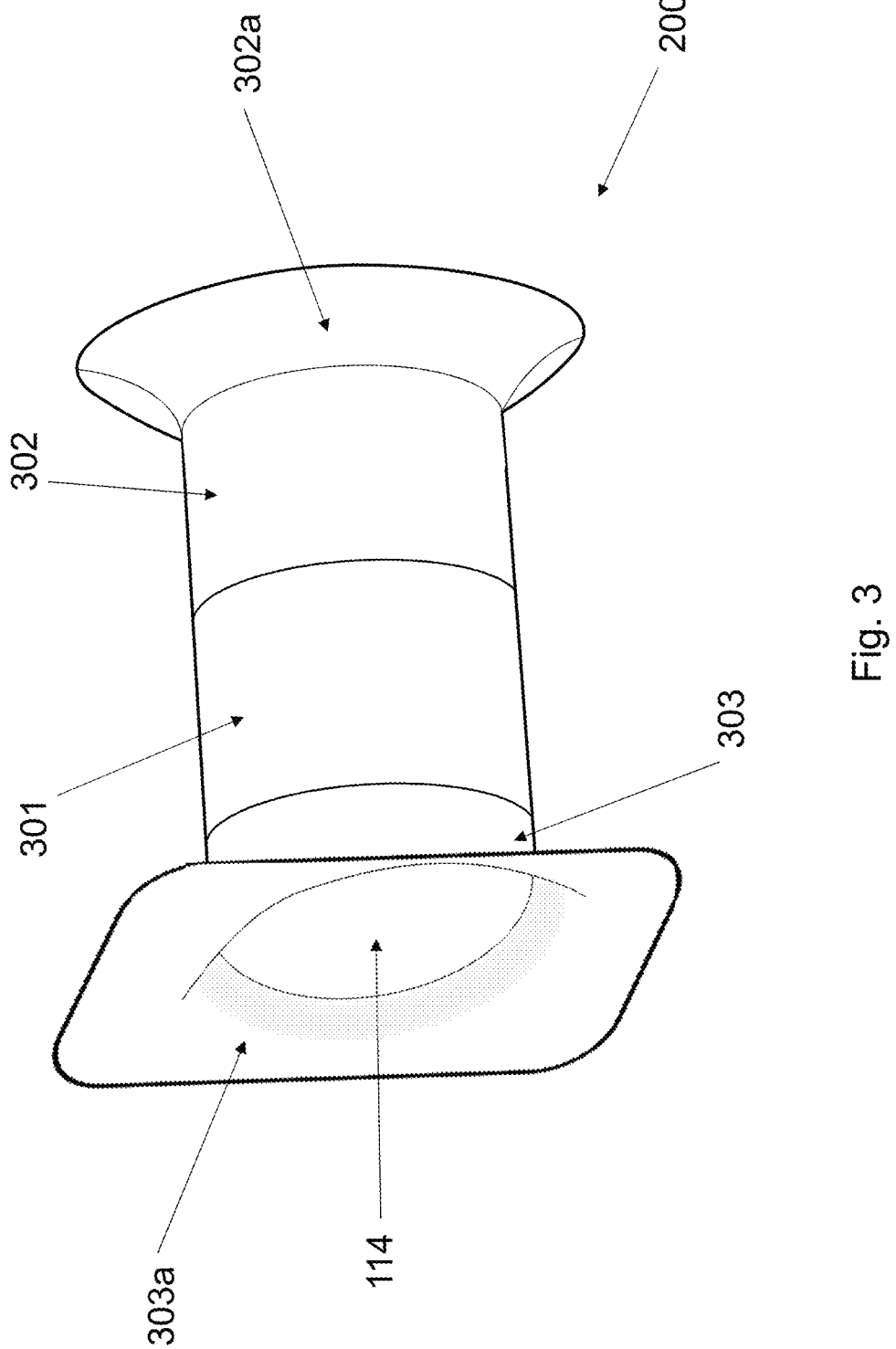
FIG. 3 depicts a bore tube according to the present disclosure.

FIG. 3 depicts a bore tube 200 according to the present disclosure. The bore tube 200 defines a bore 114. The bore tube 200 comprises a first section 301 and a second section 302. The first section 301 is formed of a first material. The second section 302 is formed of a second material.

In some embodiments, the bore tube 200 may be substantially cylindrical. The first section 301 may also be substantially cylindrical. The first section 301 may be a truncated cylinder portion of the cylindrical bore tube 200. The second section 302 may comprise a substantially cylindrical portion and/or a truncated cylinder portion and may comprise a funnel-shaped portion 302a. The funnel-shaped portion 302a may provide a smooth transition between the inner surface of the bore tube 200 and an external façade of the radiotherapy device.

The source of imaging radiation and the detector (not shown in FIG. 3) may be aligned with the first section 301 of the bore tube 200. In other words, the source of imaging radiation and the detector may each be at a corresponding longitudinal position along the length of the bore tube 200 to the first section 301. In the embodiment shown in FIG. 3, the first section 301 is the section through which the imaging radiation passes during an imaging process. Specifically, the source of imaging radiation and the detector may be aligned with the section of the bore tube 200 through which the imaging radiation passes. A treatment radiation beam for radiotherapy may also pass, at least in part, through the first section 301.

The first section 301 may attenuate an imaging radiation beam (not shown in FIG. 3) by a first attenuation level. The second section 302 may attenuate an imaging radiation beam by a second attenuation level. The first attenuation level may be lower than the second attenuation level. The imaging radiation beam passes through the bore tube 200 twice before reaching the detector: once passing from the source to the patient (i.e. entering the bore 114) and again passing from the patient to the detector (i.e. leaving the bore 114). Therefore the first section 301 may attenuate an imaging radiation beam firstly when the beam enters the bore 114, and additionally when the beam leaves the bore 114 to reach the detector. The first attenuation level for the first section 301 may account for this two-fold attenuation, i.e. may describe the total attenuation of the imaging beam caused by passing through the bore tube 200 twice. The first attenuation level may be lower than 10%. The first attenuation level may be approximately 5%. The first total attenuation level may be lower than 5%.

The first material forming the first section 301 may comprise a different material composition to the second material forming the second section 302. The first section 301 may comprise the same or similar materials to the second section 302 in different quantities and/or in different arrangements.

A bore tube with a first section and a second section gives the ability to configure the sections individually to different requirements/functions. For example, optionally the first material forming the first section 301 and second material forming the second section 302 may be different materials.

Being able to configure, or 'tailor', the sections individually provides several advantages over a single, uniform bore tube. The section of the bore tube 200 through which the imaging radiation passes has strict property requirements in order to achieve very high quality imaging, for example one or more of low attenuation levels, resilience to radiation exposure, thermal properties, rigidity, optical transparency, flexibility, strength, durability, attenuation homogeneity and/or lack of defects and artefacts. To achieve all the necessary properties, the material for the section of the bore tube 200 through which imaging radiation passes must be highly engineered, precisely manufactured and rigorously tested. This can be expensive and labour-intensive. By segmenting the bore, the section through which the imaging radiation passes can be tailored to these particular properties whilst allowing the rest of the bore tube to be optionally configured differently or optionally provide different properties. In particular, the requirements for the first total attenuation level can be met by the first section of the bore tube in order to achieve high quality imaging, whilst the second section may not need to meet these same requirements. This allows versatility of the bore tube and can reduce the overall cost and labour associated with fabricating the bore tube, whilst greatly improving image quality. In other words, the present disclosure provides an improved design for a bore tube of a radiotherapy device which improves imaging quality.

A further advantage of segmenting the bore tube 200 into a first section 301 and a second section 302 is that the bore tube 200 can still provide a physical barrier between a patient and fast-moving components of the radiotherapy device along the whole length of the bore tube 200 (as opposed to, for example, reducing attenuation by simply creating a 'hole' in the bore tube). This prevents intimidation of the patient as the components of the radiotherapy device are out of sight, and also avoids parts of the patient becoming trapped or pinched between the patient table (not shown in FIG. 3) and the fast-moving components.

The first section 301 may be joined to the second section 302 at an interface or joint configured to enable decoupling and recoupling of the first section 301 and second section 302. Segmenting the bore tube 200 into sections which may be decoupled and recoupled enables repair, maintenance and replacement of the sections to be carried out independently, which avoids the need for replacement of the entire bore tube to fix a regional fault. The bore tube will be easier to transport and handle in sections rather than as a whole. Easy repairs, maintenance, installation and dismantling of the bore tube reduces downtime of the radiotherapy device.

The decoupling and recoupling of the first section 301 and second section 302 may be enabled via a joint mechanism at the interface between the sections 301, 302. The joint mechanism may be configured such that decoupling/recoupling can be performed quickly and easily by one person. The joint mechanism may comprise guide geometry to prevent misalignment when recoupling the sections 301, 302. The joint mechanism may engage with the first section 301 and the second section 302 and guide the sections 301, 302 towards one another for recoupling, and away from each other for decoupling.

The joint mechanism may comprise a latch mechanism. The joint mechanism may comprise a plurality of latch mechanisms situated at various positions around the circumference of the bore tube 200 at the interface between the first section 301 and the second section 302. Any suitable latch mechanism may be used, such as but not limited to a spring latch, and/or a toggle latch.

In alternative embodiments, the joint mechanism may comprise a screw which can be fastened for recoupling and unfastened for decoupling. The fastening and/or unfastening of the screw may comprise a simple pull/push action. The joint mechanism may comprise a plurality of screws situated at various positions around the circumference of the bore tube 200 at the interface between the first section 301 and the second section 302.

These joint mechanisms may advantageously enable particularly fast, simple and/or accurate coupling and decoupling of the respective sections 301, 302 of the bore tube 200.

In some embodiments, the bore tube 200 may have an internal diameter of approximately 1 m.

The first section 301 may be disposed in a first region from a first point along the length of the bore tube 200 to a second point along the length of the bore 200. The first section 301 of the bore tube 200 may be longitudinally adjacent to the second section 302 of the bore tube 200. The first section 301 may be disposed around the circumference of the bore. The first section 301 may extend along the central axis of the bore by a first length. That is, the distance between the first point along the length of the bore and the second point along the length of the bore may be referred to as a first length. The first length should be arranged such that the first section provides protection to the patient from the fast-moving components of the radiotherapy device. The first length may be a fraction of the total length of the bore. The first length may be approximately half the total length of the bore or the bore tube 200. In an example embodiment, the first length may be between a half and a quarter of the total length of the bore or the bore tube 200. In another example embodiment, the first length may be between a third and a quarter of the total length of the bore or the bore tube 200. The first length may be at least a tenth, ninth, eight, seventh, sixth, fifth, quarter, third or half the total length of the bore or bore tube 200. The first length may be approximately 0.3 m, approximately 0.4 m, approximately 0.5 m, approximately 0.6 m, approximately 0.7 m, approximately 0.8 m, approximately 0.9 m or approximately 1 m.

As depicted in FIG. 2, the area of the imaging beam incident on the detector 206 (not shown in FIG. 3) is larger than the area of the imaging beam first passing through the bore tube 200 upon entry into the bore 114. Therefore the first section 301 of the bore tube 200 needing to be completely, mostly or predominantly transparent to imaging radiation may extend far enough along the central axis of the bore 114 so as to enable transmission of the beam 205 across the whole area, rather than just, for example, a central portion of the beam. In other words, the first portion 301 may be dimensioned such that the whole cross section of the imaging beam is configured to pass through the first portion 301. The length of the first section 301 may therefore depend on one or more of the diameter of the bore 114 or gantry 104, the shape of the imaging radiation beam 205 and the size of the detector 206. Depending on these parameters, a length of the first section 301 of approximately 500 mm-600 mm, for example approximately 500 mm, 510 mm, 520 mm, 530 mm, 540 mm, 550 mm, 560 mm, 570 mm, 580 mm, 590 mm or 600 mm may be implemented. The length of the first section 301 may be optimised such that it is large enough for imaging radiation to pass therethrough but no larger, or not much larger, in order for the remainder of the bore tube 200 to be engineered to meet other requirements of the bore tube or to be manufactured according to less rigorous requirements. In some examples, the bore tube 200 may comprise or consist of a single (integrally formed and/or unjointed)

section formed of a material described herein extending along the whole length or substantially the whole length of the bore tube 200, e.g. along an extent of the bore tube 200 along which the bore tube 200 is cylindrical or substantially cylindrical in shape.

In some embodiments, the radiotherapy device may be configured to carry out cone beam computed tomography (CBCT). Again, for a cone-shaped imaging radiation beam, the area of the beam incident on the detector 206 (not shown in FIG. 3) is larger than the area of the imaging beam first passing through the bore tube 200 upon entry into the bore 114. This can be seen in FIG. 2. The length of the first portion 301 may be determined based on the size of the beam cone. In particular, the length of the first portion 301 may be determined at least based on the size of the area of the beam cone which must pass through the bore tube 200 when leaving the bore 114 passing from the patient 108 to the detector 206. Additionally or alternatively, the length of the first portion 301 may be determined based on the size of the detector 206. The first portion 301 may be dimensioned, and the imaging apparatus may be arranged, such that the imaging beam passes through the first portion 301 and does not pass through the second portion 302, i.e. such that the whole cross section of the imaging beam passes through the first portion 301.

In some embodiments, optionally, the bore tube 300 may further comprise a third section 303. The third section 303 may be formed of a third material. The third section 303 may attenuate the imaging radiation beam by a third attenuation level. In some examples, the third section 303 may be formed of the same material as the second section 302.

The first section 301 may optionally comprise a different material composition, and optionally or additionally provide different material properties, to the second section 302, and/or the optional third section 303. The second section 302 may optionally comprise a different material composition, and optionally or additionally provide different material properties, to the optional third section 303.

In high quality imaging, it is desirable to be able to see fine detail in low contrast objects. Therefore, it is advantageous to provide a substantially homogeneous and/or isotropic material composition for the first section such that there are few/no artefacts and/or variations in the material. This enables increased contrast resolution of images and reduces noise from the internal structure of the bore material. Examples of suitable materials providing substantial homogeneity and/or isotropy may include, and are not limited to, polycarbonate, polymethyl methacrylate (PMAA), other plastics or metals.

The first section 301 may comprise a composite material. The composite material may comprise fibers. The composite material may comprise a resin matrix. The resin matrix may comprise an epoxy resin. The composite material may comprise a plurality of fibers, optionally arranged in a fiber structure, and a resin matrix. The fibers may comprise carbon and/or other carbon-based materials. Use of fiber materials with a relatively low atomic number may advantageously enable reduced attenuation and improved imaging. The fibers may comprise aramid. The fibers may comprise glass. The fibers may attenuate the imaging radiation beam by a fiber attenuation level. The resin may attenuate the imaging radiation beam by a resin attenuation level. The fiber attenuation level and the resin attenuation level may be substantially similar. The difference between the fiber attenuation level and the resin attenuation level may be less than 1%. In a preferred embodiment, the difference may be approximately 0.5%. Minimising the difference in attenuation caused by the fibers vs the resin enables increased contrast resolution of images and reduces noise from the internal structure of the bore material.

In an example embodiment, the first section 301 may comprise a composite material. The composite material may comprise a plurality of fibers, optionally carbon fibers, arranged in a fiber structure, and a resin matrix optionally comprising an epoxy resin. The fiber structure may comprise a plurality of fiber layers in a predefined pattern, and/or the fibers may be arranged in a particular orientation. This enables uniformity and substantial homogeneity of the composite material such that the effect of any attenuation differences between the fibers and the matrix is minimised. In this way, contrast resolution of images is increased and noise from the internal structure of the bore material is reduced.

The fiber structure may be interspersed within the resin matrix, such that resin of the resin matrix may be present between at least some of the plurality of fibers of the fiber structure. Each fiber of the plurality of fibers may be uniform in shape and size, or there may be a variation in diameter between individual fibers. The fiber arrangement and/or orientation within the fiber structure may be optimized to minimise differences in attenuation between the plurality of fibers and the resin matrix, and/or between fibers of different materials. The fiber structure may comprise a plurality of layers of fibers, wherein each layer comprises a plurality of fibers placed in a predefined pattern. At least one of the diameter, orientation and/or pattern arrangement of the fibers arranged within each layer may be varied, such that the plurality of fibers of a single layer may comprise different diameters, orientations and/or patterns. Additionally or alternatively, at least one of the diameter, orientation and/or pattern of the plurality of fibers of each layer may be varied between layers, such that within a single layer the fibers are substantially uniform in size and/or shape whilst the size and/or shape of fibers varies between layers.

The second section 302 may be disposed in a second region from the second point along the length of the bore 300 to a third point along the length of the bore. The second section 302 may comprise a first funnel-shaped portion 302a. The first funnel-shaped portion 302a may provide a substantially smooth transition between the inner surface of the bore tube 300 and an external façade of the radiotherapy device.

The third section 303 may comprise a second funnel-shaped portion 303a. The second funnel-shaped portion 303a may provide a substantially smooth transition between the inner surface of the bore tube 300 and an external façade of the radiotherapy device.

For a bore tube segmented into a first, a second and a third section, the section through which the imaging radiation passes may optionally be located between the other two sections. For example, in the exemplary embodiment shown in FIG. 3, the first section is between the second section and the third section. In particular, the third section may be disposed in a third region from the first point along the length of the bore 114 to a fourth point along the length of the bore 114. In an embodiment such as that shown in FIG. 3, where the first section 301 through which the imaging radiation passes is located between the second and third sections 302, 303, the third section 303 may be joined to the first section at a joint (similar to the joint described above) configured to enable decoupling and recoupling of the first section 301 and the third section 303.

Alternatively, the third section may be disposed adjacent to the second section, i.e. with the second section 302 between the first section 301 and the third section 303. In such embodiments, the third section 303 may be joined to the second section at a joint (similar to the joint described above) configured to enable decoupling and recoupling of the second section 302 and third section 303.

The bore tube 200 may be assembled by joining the first and second section (and optionally the third section) to form one structure. The interface between the respective sections may be a substantially smooth transition from one section to the next.

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The disclosure comprises the following items:

1. A radiotherapy device comprising:
a rotatable gantry; and
a bore tube defining a bore, wherein the bore tube comprises:
a first section formed of a first material; and
a second section formed of a second material.

2. The radiotherapy device of item 1, wherein the first section is configured to attenuate an imaging radiation beam by a first attenuation level, and the second section is configured to attenuate the imaging radiation beam by a second attenuation level.

3. The radiotherapy device of item 2, wherein the first attenuation level is lower than the second attenuation level.

4. The radiotherapy device of any preceding item, wherein the first section is disposed in a first region from a first point along the length of the bore to a second point along the length of the bore, and the second section is disposed in a second region from the second point along the length of the bore to a third point along the length of the bore.

5. The radiotherapy device of any preceding item, wherein the first section is disposed around the circumference of the bore.

6. The radiotherapy device of any preceding item, wherein each of the first section and the second section are substantially cylindrical.

7. The radiotherapy device of any preceding item, wherein the first section is joined to the second section at a joint configured to enable decoupling and recoupling of the first section and the second section.

8. The radiotherapy device of any preceding item, wherein the radiotherapy device comprises an imaging apparatus comprising a source of imaging radiation and a detector.

9. The radiotherapy device of item 8, wherein the source of imaging radiation and the detector are aligned with the first section of the bore tube.

10. The radiotherapy device of item 8 or item 9, wherein the source of imaging radiation is configured to emit kV X-rays and the detector is configured to detect kV X-rays.

11. The radiotherapy device of any of items 8-10, wherein the imaging apparatus is configured for cone beam computed tomography, and wherein the first section extends along a central axis of the bore by a first length arranged such that a cone beam emitted from the source of imaging radiation and received by the detector is arranged to pass through the first section without passing through the second section.

12. The radiotherapy device of item 11, wherein the first length is between a half and a quarter of a total length of the bore, and optionally wherein the first length is in the range 500-600 mm.

13. The radiotherapy device of any preceding item, wherein the first section comprises a composite material.

14. The radiotherapy device of item 13, wherein the composite material comprises fibers and a resin matrix.

15. The radiotherapy device of item 14, wherein the fibers are arranged in a fiber structure.

16. The radiotherapy device of any preceding item, wherein the first attenuation level is lower than 10%, and optionally wherein the first attenuation level is lower than 5%.

17. The radiotherapy device of any preceding item, wherein the bore tube comprises a third section and optionally wherein the third section attenuates the imaging radiation beam by a third attenuation level.

18. The radiotherapy device of any preceding item, further comprising a joint mechanism for decoupling and recoupling the first section and the second section.

19. The radiotherapy device of item 18, wherein the joint mechanism comprises at least one latch mechanism.

20. The radiotherapy device of item 18 or item 19, wherein the joint mechanism comprises at least one screw.

What is claimed is:

1. A radiotherapy device comprising:
a rotatable gantry;
a bore tube defining a bore, wherein the bore tube comprises:
a first section formed of a first material; and
a second section formed of a second material, wherein the first section is disposed in a first region from a first location along a length of the bore to a second location along the length of the bore, and the second section is disposed in a second region from the second location along the length of the bore to a third location along the length of the bore; and
an imaging apparatus comprising a source of imaging radiation and a detector, the source of imaging radiation and the detector being aligned with the first section of the bore tube.

2. The radiotherapy device of claim 1, wherein the first section is configured to attenuate an imaging radiation beam by a first attenuation level, and the second section is configured to attenuate the imaging radiation beam by a second attenuation level.

3. The radiotherapy device of claim 2, wherein the first attenuation level is lower than the second attenuation level.

4. The radiotherapy device of claim 2, wherein the first attenuation level is lower than 10%.

5. The radiotherapy device of claim 2, wherein the bore tube comprises a third section, and wherein the third section attenuates the imaging radiation beam by a third attenuation level.

6. The radiotherapy device of claim 1, wherein the first section is disposed around a circumference of the bore.

7. The radiotherapy device of claim 1, wherein each of the first section and the second section are substantially cylindrical.

8. The radiotherapy device of claim 1, wherein the first section is joined to the second section at a joint configured to enable decoupling and recoupling of the first section and the second section.

9. The radiotherapy device of claim 1, wherein the source of imaging radiation is configured to emit kilovolt (kV) X-rays and the detector is configured to detect kV X-rays.

10. The radiotherapy device of claim 1, wherein the imaging apparatus is configured for cone beam computed tomography, and wherein the first section extends along a central axis of the bore by a first length arranged such that a cone beam emitted from the source of imaging radiation and received by the detector is arranged to pass through the first section without passing through the second section.

11. The radiotherapy device of claim 10, wherein the first length is between a half and a quarter of a total length of the bore, and wherein the first length is between 500 mm-600 mm, inclusive.

12. The radiotherapy device of claim 1, wherein the first section comprises a composite material.

13. The radiotherapy device of claim 12, wherein the composite material comprises fibers and a resin matrix.

14. The radiotherapy device of claim 13, wherein the fibers are arranged in a fiber structure.

15. The radiotherapy device of claim 1, further comprising:

a joint mechanism for decoupling and recoupling the first section and the second section.

16. The radiotherapy device of claim 15, wherein the joint mechanism comprises at least one latch mechanism.

17. The radiotherapy device of claim 15, wherein the joint mechanism comprises at least one screw.

18. The radiotherapy device of claim 1, wherein the first section and the second section are arranged longitudinally adjacent to each other and are joined to each other at an interface, and wherein the first section extends from the first location to the second location and the second section extends from the second location to the third location.

\* \* \* \* \*